United States Patent [19]

Akamatsu

[11] Patent Number: 5,300,669
[45] Date of Patent: Apr. 5, 1994

[54] METHYLPHENETHYL FUNCTIONAL SILICONES

[75] Inventor: Shoji Akamatsu, Chiba, Japan

[73] Assignee: Dow Corning Toray Silicone Co., Ltd., Tokyo, Japan

[21] Appl. No.: 975,046

[22] Filed: Nov. 12, 1992

[30] Foreign Application Priority Data

Nov. 28, 1991 [JP] Japan ................................ 3-339875
Nov. 29, 1991 [JP] Japan ................................ 3-342023

[51] Int. Cl.$^5$ .............................................. C07F 7/08
[52] U.S. Cl. ...................................... 556/453; 556/456; 359/228; 359/642; 359/831; 430/321; 385/77; 385/147
[58] Field of Search ................ 556/453, 456; 358/225, 358/901; 359/228; 430/321

[56] References Cited

U.S. PATENT DOCUMENTS 3,088,964  5/1963  Ryan .................................. 556/453
4,395,527  7/1983  Berger ................................ 528/26

FOREIGN PATENT DOCUMENTS 129293 of 1980 Japan .
195389 of 1987 Japan .

*Primary Examiner*—Paul F. Shaver
*Attorney, Agent, or Firm*—James L. DeCesare

[57] ABSTRACT

An optical matching oil that is immune to timewise variations in its refractive index, that undergoes little increase in viscosity below room temperature, and that also resists crystallization below room temperature. The optical matching oil is based on an organosilicon compound with the following general formula

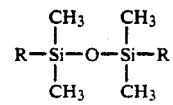

wherein R is selected from the group consisting of methyl, vinyl, and 2-methylphenethyl with the proviso that at least one R group is the 2-methylphenethyl group.

6 Claims, 5 Drawing Sheets

METHYLPHENETHYL FUNCTIONAL SILICONES

BACKGROUND OF THE INVENTION

The present invention relates to an optical matching oil. More specifically, the present invention relates to an optical matching oil that consists of an organosilicon compound whose molecule contains at least one 2-methylphenethyl group.

Like optical adhesives and optical greases, optical matching oils are employed as filling agents between the lens and prisms present in optical devices and as filling agents in optical fiber connectors. When air bubbles remain in the optical matching oil filled between lenses, between prisms, or between the ends of optical fibers, or when air bubbles are generated at the contact surface between an optical matching oil and a lens, prism, or optical fiber terminus, the transmitted light or optical signal is scattered, causing a flare or transmission loss. As a consequence, one type of optical matching oil in use up to now has been based on a low-viscosity phenylsilicone oil having a viscosity of 10 to 100 centistokes and a refractive index of 1.46 to 1.51.

However, phenylsilicone oils by themselves have relatively high viscosities and must therefore be diluted with low-molecular-weight silicone oils, such as, dimethylsilicone oils. This has created the problem of a timewise variation in the refractive index of the optical matching oil due to volatilization of the low-molecular-weight silicone oil. Another problem is associated with the use of such optical matching oils in ambients below room temperature. This type of optical matching oil suffers from a deterioration in performance in such ambients due to a sharp increase in the viscosity of the phenylsilicone oil base or even crystallization of part of the phenylsilicone oil. For these reasons, there is a need for an optical matching oil that is immune to timewise variations in its refractive index, that presents little increase in viscosity below room temperature, and that resists crystallization below room temperature.

SUMMARY OF THE INVENTION

The present invention takes as its object the introduction of an optical matching oil that is immune to timewise variations in its refractive index, that undergoes little increase in viscosity below room temperature, and that also resists crystallization below room temperature.

DETAILED DESCRIPTION OF THE INVENTION

Figure 1:
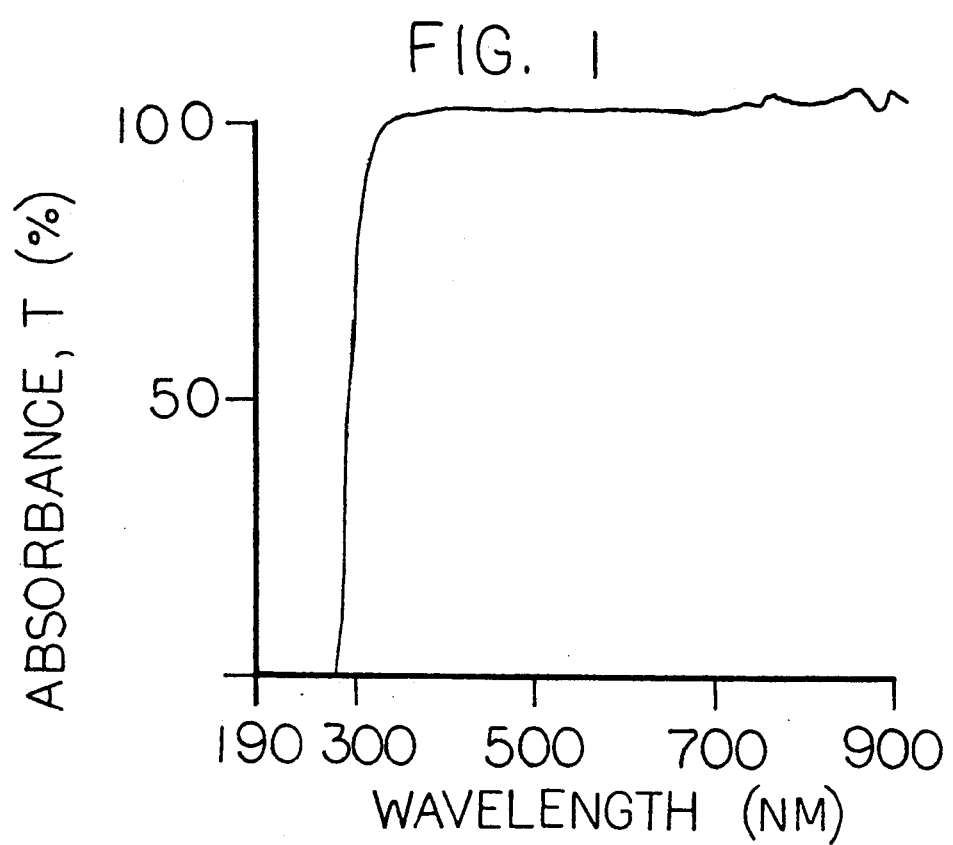
FIG. 1 is a light transmittance chart for the 1-(2-methylphenethyl)-3-vinyltetramethyldisiloxane prepared in Reference Example 1.
Figure 2:
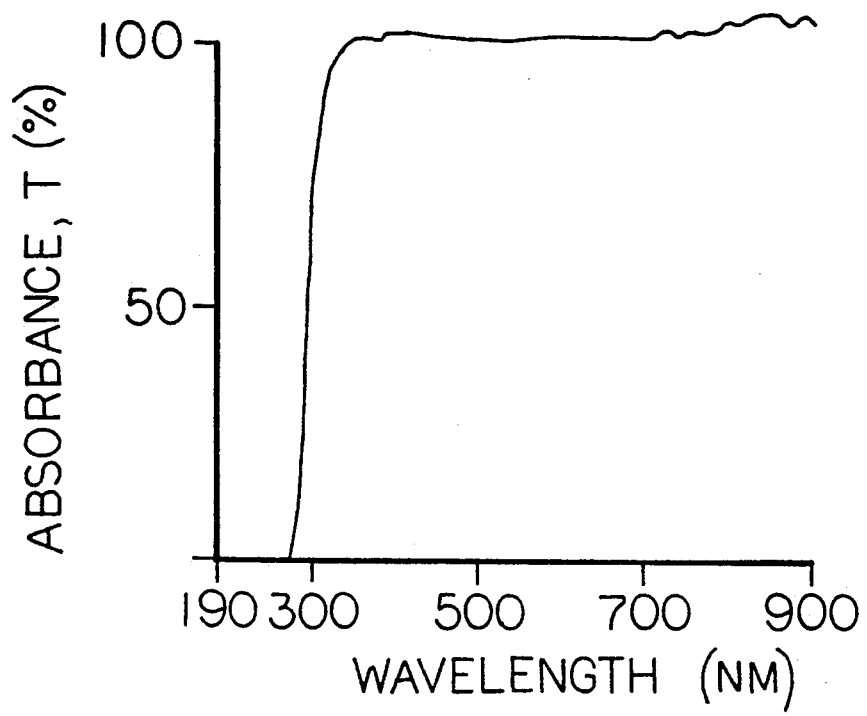
FIG. 2 is a light transmittance chart for the 2-methylphenethylpentamethyldisiloxane prepared in Reference Example 2.
Figure 3:
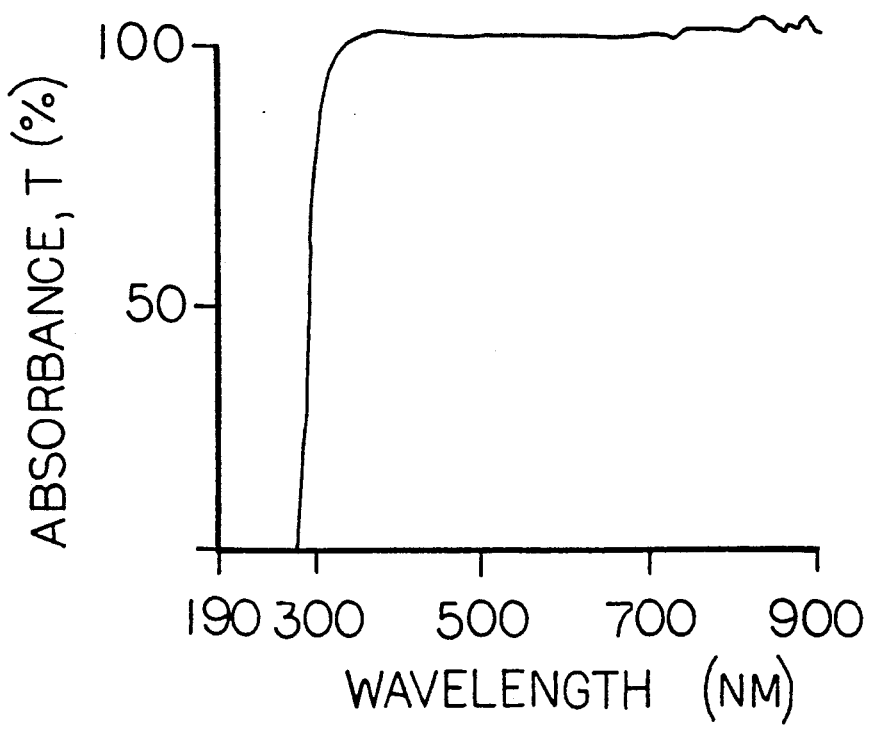
FIG. 3 is a light transmittance chart for the 1,3-di(2-methylphenethyl)tetramethyldisiloxane prepared in Reference Example 3.
Figure 4:
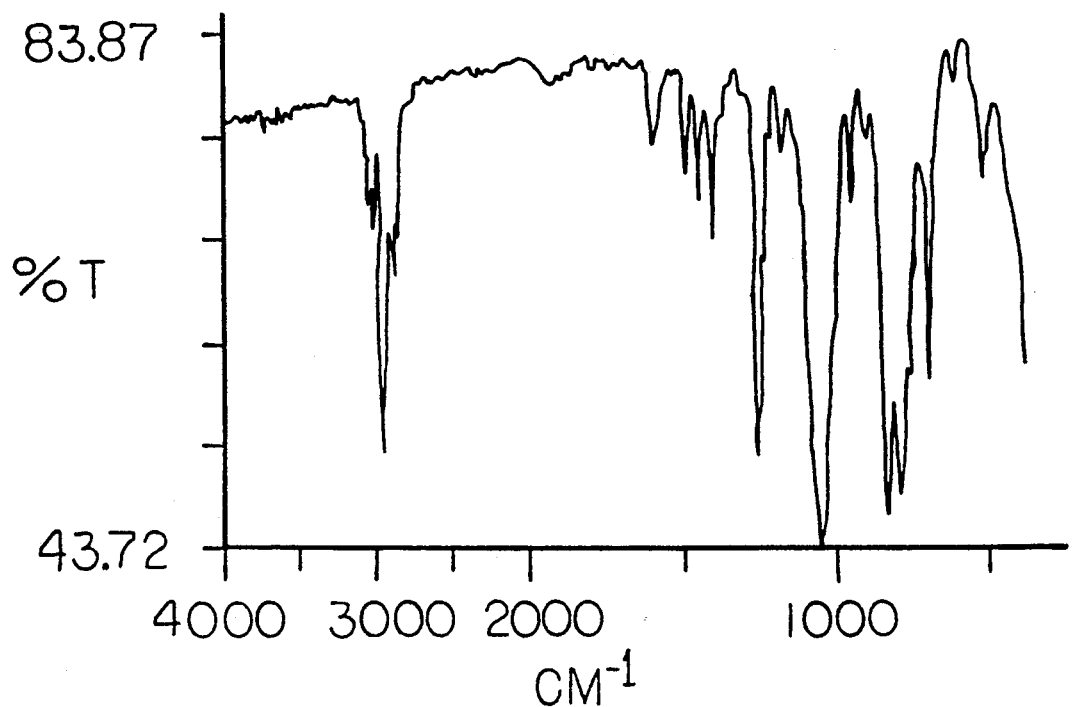
FIG. 4 contains an infrared absorption spectrogram for the 1-(2-methylphenethyl)-3-vinyltetramethyldisiloxane synthesized in Reference Example 1.
Figure 5:
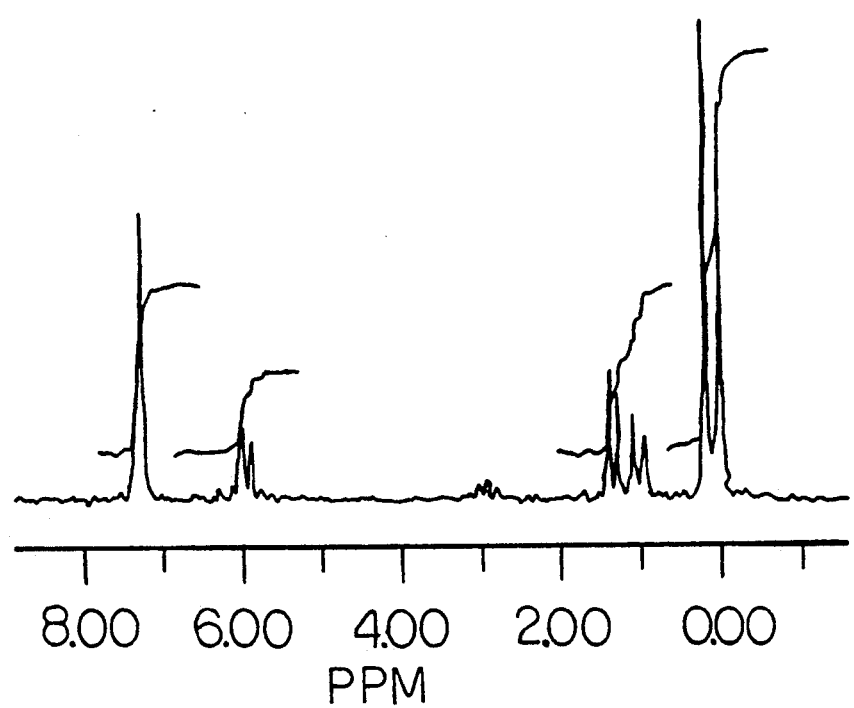
FIG. 5 contains a $^1$H nuclear magnetic resonance spectrogram for the 1-(2-methylphenylethyl)-3-vinyltetramethyldisiloxane synthesized in Reference Example 1.
Figure 6:
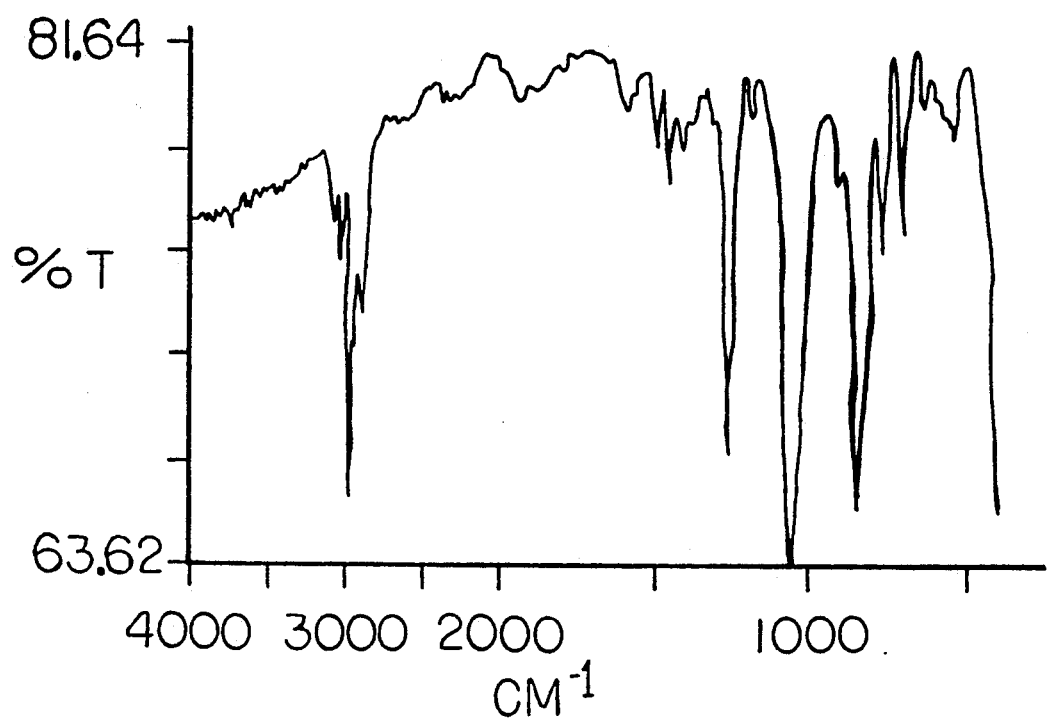
FIG. 6 contains an infrared absorption spectrogram for the 2-methylphenylethylpentamethylsiloxane synthesized in Example 4.
Figure 7:
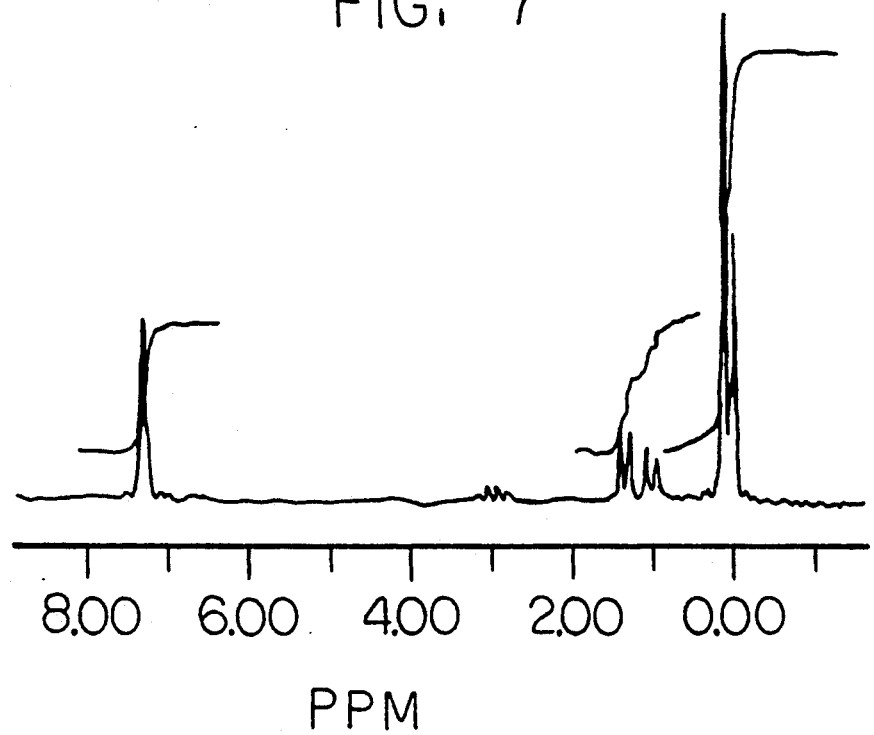
FIG. 7 contains a $^1$H nuclear magnetic resonance spectrogram for the 2-methylphenethylpentamethyldisiloxane synthesized in Example 4.
Figure 8:
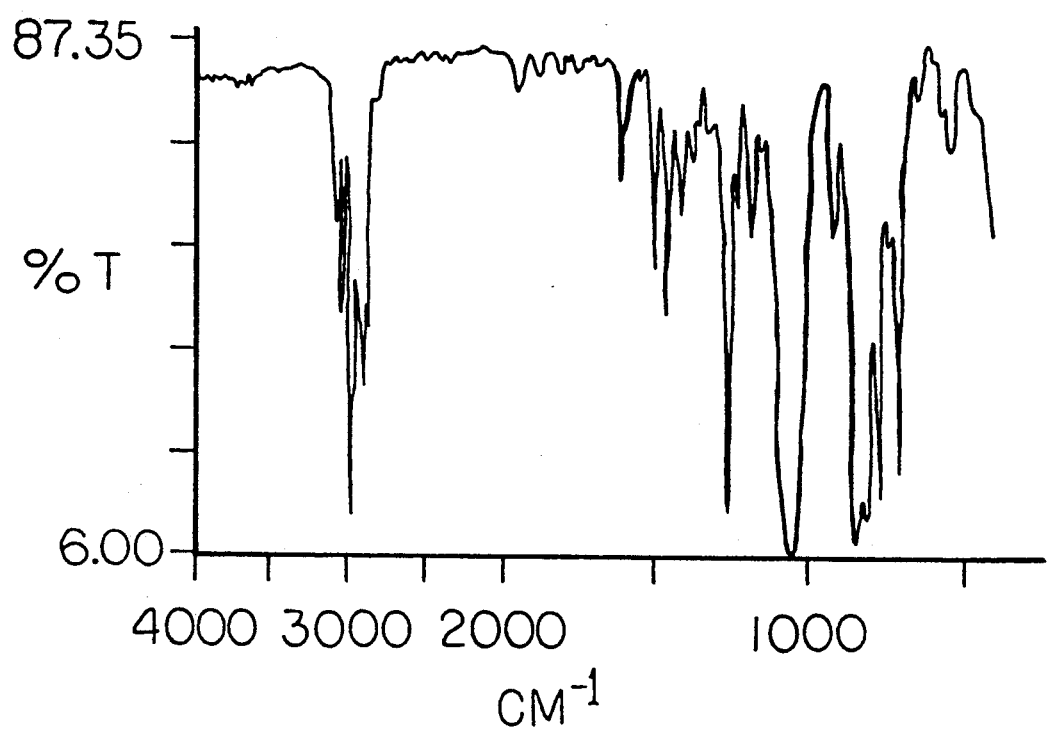
FIG. 8 contains an infrared absorption spectrogram for the 1,3-di(2-methylphenethyl)tetramethyldisiloxane synthesized in Example 5.
Figure 9:
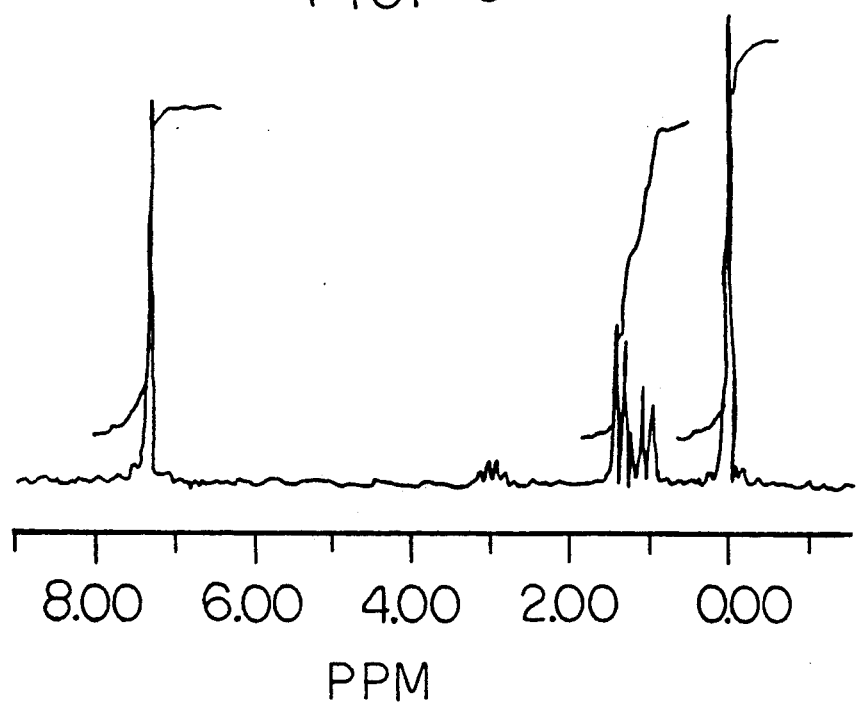
FIG. 9 contains a $^1$H nuclear magnetic resonance spectrogram for the 1,3-di(2-methylphenethyl)tetramethyldisiloxane synthesized in Example 5.

The optical matching oil according to the present invention comprises an optical matching oil based on an organosilicon compound with the following general formula

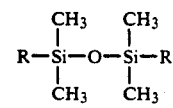

wherein R is selected from the group consisting of methyl, vinyl, and 2-methylphenethyl with the proviso that at least one R group is the 2-methylphenethyl group.

The optical matching oil of the present invention is based on the aforesaid organosilicon compound that contains at least one 2-methylphenethyl group in each molecule, and this organosilicon compound is exemplified by 1-(2-methylphenethyl)-3-vinyltetramethyldisiloxane, 2-methylphenethylpentamethyldisiloxane, and 1,3-di(2-methylphenethyl)tetramethyldisiloxane. These organosilicon compounds have viscosities in the range of 1 to 10 centistokes and refractive indexes in the range of 1.46–1.51. In particular, because they have relatively high boiling points, optical matching oils based on these organosilicon compounds do not suffer from timewise variations in refractive index. These organosilicon compounds are also characterized by their low viscosity increase at temperatures below room temperature and by their resistance to crystallization at temperatures below room temperature, for example, at −10° C. Another characteristic of the optical matching oils of the present invention based on such organosilicon compounds is their transparency in the visible region (450 to 750 nm) and also in the near infrared region.

The synthesis of the organosilicon compounds comprising the base or principal agent of the optical matching oil of the present invention is exemplified by the following methods:

(a) the addition reaction of 1,1,3,3-tetramethyldisiloxane with alpha-methylstyrene under platinum catalysis, (b) the re-equilibration reaction between the 1,3-di(2-methylphenethyl)tetramethyldisiloxane prepared as in (a) with 1,3-divinyltetramethyldisiloxane or hexamethyldisiloxane, and (c) the cohydrolysis of 2-methylphenethyldimethylhalosilane with a halosilane selected from the group consisting of trimethylhalosilane, vinyldimethylhalosilane, and 2-methylphenethyldimethylhalosilane.

Chloroplatinic acid, alcohol solutions of chloroplatinic acid, platinum/olefin complexes, platinum/vinylsiloxane complexes, and platinum-on-inorganic powder, are examples of the platinum group metal catalysts that can be deployed in the above-listed platinum-catalyzed addition reaction (a) between 1,1,3,3-tetramethyldisiloxane and alpha-methylstyrene.

With regard to the re-equilibration reaction (b) between 1,3-di(2-methylphenethyl)tetramethyldisiloxane and 1,3-divinyltetramethyldisiloxane or hexamethyldisiloxane, the hexamethyldisiloxane and 1,3-divinyltetramethyldisiloxane used in this method are available commercially while the 1,3-di(2-methylphenethyl)tetramethyldisiloxane can be synthesized by the method already described above. An acid or base catalyst can be used as the re-equilibration catalyst. Operable acid catalysts are specifically exemplified by mineral acids such as hydrochloric acid, sulfuric acid, nitric acid, and by solid catalysts such as activated clay, and Filtrol. Operable base catalysts are specifically exemplified by lithium hydroxide, sodium hydroxide, potassium hydroxide, cesium hydroxide, tetramethylammonium hydroxide, lithium silanolate, potassium silanolate, phenyllithium, methyllithium, and butyllithium. The quantities of addition of hexamethyldisiloxane or 1,3-divinyltetramethyldisiloxane and 1,3-di(2-methylphenethyl)tetramethyldisiloxane are not critical however, preferred amounts are 0.1 to 10 moles hexamethyldisiloxane or 1.3-divinyltetramethyldisiloxane per 1 mole 1,3-di(2-methylphenethyl)tetramethyldisiloxane. The preparative conditions are also not critical, but a preferred range for the reaction temperature is 50° to 200° C.

With regard to the method comprising the cohydrolysis of 2-methylphenethyldimethylhalosilane with a halosilane selected from the group consisting of trimethylhalosilane, vinyldimethylhalosilane, and 2-methylphenethyldimethylhalosilane, the trimethylhalosilane and vinyldimethylhalosilane are available commercially while the 2-methylphenethyldimethylhalosilane can be prepared by an addition reaction between dimethylhalosilane and alpha-methylstyrene under platinum catalysis. The reaction temperature is not critical, and the reaction can be run, for example, in the temperature range of from room temperature to the boiling point of the particular halosilane or the boiling point of any organic solvent used. An organic solvent can be used in the reaction, and operable organic solvents are exemplified by aromatic solvents such as toluene, and xylene, and aliphatic solvents such as hexane, heptane, and octane. In addition, this halosilane cohydrolysis is preferably run with the addition of a basic salt such as sodium carbonate, potassium carbonate, calcium carbonate, sodium bicarbonate, or an amine compound such as trimethylamine, and triethylamine, in order to capture the hydrogen chloride by-product.

The optical matching oil of the present invention is based on the aforesaid organosilicon compound whose molecule contains at least one 2-methylphenethyl group. The optical matching oil of the present invention may consist of only this organosilicon compound, or it may also contain other components, for example, additives such as antioxidants, and refractive-index regulators. Blendable antioxidants are exemplified by 4,4'-thiobis(6-tert-butyl-m-cresol),4,4'-butylidenebis (6-tert-butyl-m-cresol), 2,2'-methylenebis(4-methyl-6-tert-butylphenol), 2,2'-methylenebis(4-ethyl-6-tert-butylphenol), 2,5-di-tertbutylhydroquinone, 2,5-di-tert-amyl hydroquinone, and 2,6-di-tert-butyl-p-cresol. Operable refractive-index regulators are exemplified by dimethylpolysiloxanes and methylphenylpolysiloxanes that contain only small quantities of volatile component and by organic refractive-index regulators.

Because the optical matching oil of the present invention has a high refractive index and low viscosity, it can be employed as a filling agent between the lenses in a video projector or as filler in optical fiber connectors. It is suitable for use in optical fiber transfer or diverter devices, optical fiber switches, and movable optical fiber connectors.

The present invention will be further explained below in the illustrative examples. In the examples, the refractive index, viscosity, and light transmittance were measured at 25° C.; the refractive index was measured using the D-line of sodium (589 nm); and the light transmittance was measured using water as the blank.

REFERENCE EXAMPLE 1

Preparation of
1-(2-methylphenethyl)-3-vinyltetramethyldisiloxane

The following were charged to a 1 L roundbottom flask equipped with a stirrer, thermometer, and addition funnel and heated to 70° C.: 375 g (3.15 mol) alpha-methylstyrene and 0.6 mL 1% isopropanolic chloroplatinic acid solution. 285 g (3.0 mol) dimethylchlorosilane was then dripped in from the addition funnel over 1 hour. The reaction was subsequently maintained at 80° C. for 1 hour and cooled. 212 g (1.0 mol) of the 2-methylphenethyldimethylchlorosilane product and 217 g (1.8 mol) dimethylvinylchlorosilane were dripped into a mixture of 300 g water and 100 g isopropyl alcohol. The resulting hydrolyzate was washed with water 3 times, the water (lower) layer was removed, and heating in vacuo produced 180 g (65% of the theoretical yield) 1-(2-methylphenethyl)-3-vinyltetramethyldisiloxane . This 1-(2-methylphenethyl)-3-vinyltetramethyldisiloxane had a refractive index of 1.471, a viscosity of 2.2 centistokes, and a boiling point of 121° C./5 mmHg.

REFERENCE EXAMPLE 2

Preparation of
2-methylphenethylpentamethyldisiloxane 2-methylphenethylpentamethyldisiloxane (71% of the theoretical yield) was prepared as in Reference Example 1 using trimethylchlorosilane in place of the vinyldimethylchlorosilane used in Reference Example 1. This 2-methylphenethylpentamethyldisiloxane had a refractive index of 1.463, a viscosity of 2.1 centistokes, and a boiling point of 120° C./10 mmHg.

REFERENCE EXAMPLE 3

Preparation of
1,3-di(2-methylphenethyl)tetramethyldisiloxane 1,3-di(2-methylphenethyl)tetramethyldisiloxane (95% of the theoretical yield) was prepared as in Reference Example 1 by omitting the vinyldimethylchlorosilane and using only the 2-methylphenethyldimethylchlorosilane. This 1,3-di(2-methylphenethyl)tetramethyldisiloxane had a refractive index of 1.505, a viscosity of 9.3 centistokes, and a boiling point of 160° C./0.5 mmHg.

EXAMPLE 4

The following were charged to a 1 L roundbottom flask equipped with stirrer, thermometer, and addition funnel and heated to 70° C: 375 g (3.15 mol) alpha-methylstyrene and 0.6 mL 1% isopropanolic chloroplatinic acid solution. 285 g (3.0 mol) dimethylchlorosilane was then dripped in from the addition funnel over 1 hour. The reaction was subsequently maintained at 80° C. for 1 hour and cooled. 212 g (1.0 mol) of the 2-methylphenethyldimethylchlorosilane product and 196 g (1.8 mol) trimethylchlorosilane were dripped into a mixture of 300 g water and 100 g isopropyl alcohol. The resulting reaction mixture was washed with water 3 times, the water (lower) layer was removed, and the reaction mixture (upper layer) was heated in vacuo to give 190 g (71% of the theoretical yield) 2-methylphenethylpentamethyldisiloxane. This 2-methylphenethylpentamethyldisiloxane had a refractive index of 1.463. a viscosity of 2.1 centistokes, and a boiling point of 120° C./10 mmHg.

EXAMPLE 5

The following were charged to a 1 L roundbottom flask equipped with stirrer, thermometer, and addition funnel and heated to 70° C: 375 g (3.15 mol) alpha-methylstyrene and 0.6 mL 1% isopropanolic chloroplatinic acid solution. 285 g (3.0 mol) dimethylchlorosilane was then dripped in from the addition funnel over 1 hour. The reaction was subsequently maintained at 80° C. for 1 hour and cooled. 424 g (2 mol) of the 2-methylphenethyldimethylchlorosilane product was dripped into a mixture of 300 g water and 100 g isopropyl alcohol. The resulting reaction mixture was washed with water 3 times, the water (lower) layer was removed, and the reaction mixture (upper layer) was heated in vacuo to give 350 g (95% of the theoretical yield) 1,3-di(2-methylphenethyl)tetramethyldisiloxane. This 1,3-di(2-methylphenethyl)tetramethyldisiloxane had a refractive index of 1.505. a viscosity of 9.3 centistokes, and a boiling point of 160° C./0.5 mmHg.

EXAMPLE 6

The following were charged to a 1 L roundbottom flask equipped with a stirrer and thermometer: 200 g 1,3-di(2-methylphenethyl)tetramethyldisiloxane as prepared in Example 3, 600 g hexamethyldisiloxane, and 5 g thoroughly dehydrated activated clay. This was followed by heating to 80° to 85° C. and stirring for 2 hours. The reaction mixture was then filtered and the filtrate was heated in vacuo to afford 170 g 2-(methylphenethylpentamethyldisiloxane.

EXAMPLE 7

The following were charged to a 1 L roundbottom flask equipped with a stirrer and thermometer: 200 g 1.3-di(2-methylphenethyl)tetramethyldisiloxane as prepared in Example 3, 600 g 1,3-divinyltetramethyldisiloxane, and 5 g thoroughly dehydrated activated clay. This was followed by heating to 80° to 85° C. and stirring for 2 hours. The reaction mixture was then filtered and the filtrate was heated in vacuo to afford 160 g 1-(2-methylphenethyl)-3-vinyltetramethyldisiloxane.

The light transmittance of the organosilicon compounds prepared in Reference Examples 1, 2, and 3 was measured using a light transmission meter with water as the blank. The optical fiber connection loss was measured on the organosilicon compounds prepared in Reference Examples 1, 2, and 3. Graded index optical fibers (core diameter=50 micrometers, clad diameter=125 micrometers) were installed in a holding plate tool having a V-shaped groove, the particular organosilicon compound was filled between the ends of the optical fibers, and measurement was then carried out. The results for the connection loss are reported in Table 1.

TABLE 1

| Sample Number | Reference Example 1 | Reference Example 2 | Reference Example 3 |
|---|---|---|---|
| connection loss (dB) | 2.0 | 1.8 | 1.5 |

The change in viscosity as a function of temperature was measured on the 2-methylphenethylpentamethyldisiloxane prepared in Reference Example 2 and on a phenylsilicone oil (methylphenylsiloxane oligomer with refractive index=1.558). These results are reported in Table 2. During this measurement, the methylphenylsiloxane oligomer exhibited a sharp increase in its viscosity at below room temperature and in fact was partially crystallized at −10° C.

TABLE 2

| Viscosity (centistokes) | Temperature (°C.) | | | | |
|---|---|---|---|---|---|
| | −10 | 0 | 10 | 25 | 50 |
| 2-methylphenethyl-pentamethyldisiloxane | 7.1 | 5.5 | 4.0 | 2.9 | 1.7 |
| methylphenylsiloxane oligomer | 800 | 232 | 108 | 41.4 | 12.5 |

Because the optical matching oil of the present invention is based on an organosilicon compound that contains at least one 2-methylphenethyl group in each molecule, it is characterized by freedom from time-dependent changes in its refractive index, by a small increase in its viscosity below room temperature, and by resistance to crystallization below room temperature.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. An organosilicon compound having the formula

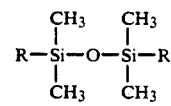

wherein one R is vinyl, and the other one R is 2-methylphenethyl.

2. A compound according to claim 1 which is 1-(2-methylphenethyl)-3-vinyltetramethyldisiloxane.

3. In an optical device having lenses, prisms, or optical fiber connectors, with an optical matching oil used as a filling agent between the lenses, prisms, or optical fiber connectors; he improvement comprising the optical matching oil being an organosilicon compound having the formula

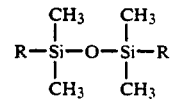

wherein R is selected from the group consisting of methyl, vinyl, and 2-methylphenethyl, and at least one R is 2-methylphenethyl.

4. The device according to claim 3 in which the compound is 1-(2-methylphenethyl)-3-vinyltetramethyldisiloxane.

5. The device according to claim 3 in which the compound is 2-methylphenethylpentamethyldisiloxane.

6. The device according to claim 3 in which the compound is 1,3-di(2-methylphenethyl)tetramethyldisiloxane.

* * * * *